United States Patent
Keinänen et al.

(12)

(10) Patent No.: US 6,235,535 B1
(45) Date of Patent: May 22, 2001

(54) FLUORESCENT ENERGY TRANSFER LIGAND INTERACTION ASSAY ON A LIPID FILM

(75) Inventors: Kari Keinänen, Espoo; Marja-Leena Laukkanen, Turku; Hans Söderlund, Espoo, all of (FI)

(73) Assignee: Valtion Teknillinen Tutkimuskeskus (FI)

( * ) Notice: Subject to any disclaimer, the term of this patent is extended or adjusted under 35 U.S.C. 154(b) by 0 days.

(21) Appl. No.: 09/202,976

(22) PCT Filed: Jun. 30, 1997

(86) PCT No.: PCT/FI97/00419

§ 371 Date: Dec. 24, 1998

§ 102(e) Date: Dec. 24, 1998

(87) PCT Pub. No.: WO98/00714

PCT Pub. Date: Jan. 8, 1998

(30) Foreign Application Priority Data

Jun. 28, 1996 (FI) .......................................... 962686

(51) Int. Cl.[7] ........................ G01N 21/76; G01N 21/64; G01N 33/53; G01N 33/543; C12N 11/18

(52) U.S. Cl. .................. 436/172; 250/458.1; 250/459.1; 250/461.1; 424/450; 435/7.1; 435/7.2; 435/7.92; 435/7.94; 435/174; 435/175; 435/440; 436/501; 436/518; 436/528; 436/532; 436/546; 436/800; 436/805; 436/819; 436/829

(58) Field of Search ............... 250/486.1, 483.1, 250/458.1, 459.1, 461.1; 422/60, 82.11, 82.07, 82.08, 82.05, 57, 58; 435/174, 968, 808, 291, 7.3, 7.33, 7.34, 7.35, 7.37, 7.36, 7.32, 7.2, 7.9, 7.92, 4, 7, 7.1, 5, 6, 320.1, 175, 7.94; 436/525, 537, 531, 805, 807, 20, 544, 530, 829, 526, 528, 534, 543, 501, 164, 172, 518, 800; 424/450; 548/159, 201; 549/220, 223, 288; 544/151, 326

(56) References Cited

U.S. PATENT DOCUMENTS

| | | | |
|---|---|---|---|
| 4,254,096 | * | 3/1981 | Monthony et al. ................... 424/8 |
| 4,598,051 | * | 7/1986 | Papahadjopoulos et al. ....... 436/512 |
| 4,605,630 | * | 8/1986 | Kung et al. ........................ 436/511 |
| 4,971,916 | * | 11/1990 | Jou et al. ............................ 436/512 |
| 5,011,771 | * | 4/1991 | Bellet et al. ....................... 435/7.94 |
| 5,094,819 | * | 3/1992 | Yager et al. ..................... 422/82.07 |
| 5,194,393 | * | 3/1993 | Hugl et al. .......................... 436/525 |
| 5,494,803 | * | 2/1996 | Carbonell et al. ................. 435/7.92 |
| 5,650,334 | * | 7/1997 | Zuk et al. ........................... 436/529 |
| 5,780,319 | * | 7/1998 | Maxfield Wilosn et al. ....... 436/518 |
| 5,945,283 | * | 8/1999 | Kwok et al. ........................... 435/6 |

FOREIGN PATENT DOCUMENTS

| | | |
|---|---|---|
| WO 89/0940 | 10/1989 | (EP) . |
| 0 429 907 B1 | 6/1991 | (EP) . |
| 0 628 819 A2 | 12/1994 | (EP) . |
| WO 95/08637 | 3/1995 | (EP) . |

OTHER PUBLICATIONS

Methods in Enzymology, vol. 246, 1995, P.R. Selvin, "Fluorescene Resonance Energy Transfer" p. 300–334.

Chem. Abstracts vol. III, 1989, W.G. Miller and F.P. Anderson 160375q.

* cited by examiner

Primary Examiner—Long V. Le
Assistant Examiner—Kartic Padmanabhan
(74) Attorney, Agent, or Firm—Evenson, McKeown, Edwards & Lenahan, P.L.L.C.

(57) ABSTRACT

This invention relates to a fluorescence-based immunoassay method for the detection of an analyte, or for the measurement of its concentration in a biological sample. The method is based on the ability of a multivalent analyte to induce aggregation of receptor molecules labeled with a fluorophore, which molecules are anchored to and are freely mobile on a lipid membrane, and thereby cause changes in the fluorescence.

11 Claims, 2 Drawing Sheets

FLUORESCENT ENERGY TRANSFER LIGAND INTERACTION ASSAY ON A LIPID FILM

This is the U.S. National Stage Application of PCT/FI97/00419 filed Jun. 30, 1997.

This invention relates to a fluorescence-based immunoassay method for the detection of an analyte, or for the measurement of its concentration in a biological sample. The method is based on the ability of a multivalent analyte to induce aggregation of receptor molecules labeled with a fluorophore, which molecules are anchored to and are freely mobile on a lipid membrane, and thereby cause changes in the fluorescence.

Traditional fluorescence-based immunoassay methods exploit the principles of the conventional immunoassay—the analyte to be measured is immobilized on a solid substrate, whereafter it is detected e.g. by using a fluorescent antibody or fluorescence-generating enzymic reaction (Hemmilä, 1991, Kricka, 1994). Advantages of a fluorescence-based assay include high sensitivity, and independence of the use of radioisotopes. The fact that like most of the other conventional immunoassays, these fluorescence-based assays are of a heterogeneous nature, i.e. the unbound antibody or antigen is separated and the analyte is determined indirectly, can be considered as a disadvantage. These washing and separating steps increase the amount of work and costs.

Fluorescence resonance energy transfer (FRET) is a physical process, in which energy from a molecular chromophore (donor, D) excited to a high energy state is transferred to another chromophore (acceptor, A) via intermolecular dipole-dipole coupling (Clegg, 1995, Selvin, 1995). A necessary prerequisite for the energy transfer is that the distance between the molecules is short (10–100 Å), that the fluorescence spectrum of the donor and the absorption spectrum of the acceptor partially overlap, and that the quantum yield of the donor ($\phi_D$), and the extinction coefficient of the acceptor ($\epsilon_A$) are high enough. FRET has been exploited to measure hybridization between nucleic acid molecules (Mergny et al., 1994) and to detect interactions between lipids and membrane proteins (Watts et al., 1986). The phenomenon has also been applied to immunoassay by labeling the antibody and antigen with fluorophores, which form a FRET donor-acceptor pair. The solution phase assay was based on the ability of the antigen (the substance to be measured) to displace the labeled antigen and thus prevent FRET phenomenon (Barnard and Walt, 1991).

Fluorescent labeling of proteins is known technology which is based on commercially available fluorophores and their derivatives (Waggoner, 1995). The fluorophores are either synthetic, relatively low-molecular organic compounds (e.g. fluorescein and rhodamine and derivatives thereof, and lanthanide chelates) or proteins (e.g. phycoerythrin and GFP, green fluorescent protein). Various parameters of the fluorescence emitted by the fluorophores can be measured: fluorescence intensity, life-time, polarization. These can also be used to monitor and quantitate the FRET phenomenon.

The Finnish patents No. 81680 and 93997 describe homogeneous immunoassay methods which use fluorescent labels. The first one of these describes a solid phase immunoassay, in which the fluorescence of the free label present in liquid phase is quenched by a light-absorbing substance, enabling the measurement of the bound label without separation steps. In the latter patent, a conventional quantitative immuno-fluorescence method is described, with the idea of achieving a sensitive assay by preventing short-lived background fluorescence. These methods have not, however, any relation to the FRET phenomenon.

Lipid bilayers are known to be structures that are spontaneously formed by phospholipids and some other polar lipids in water solution. In these, the polar heads of the lipid molecules are in contact with water (outwards), whereas the nonpolar hydrocarbon chains are oriented inwards. Planar lipid membranes can be prepared by using e.g. Langmuir-Blodgett technique (Arya et al., 1985, Zasadzinski et al., 1994) and transferred onto a solid substrate (Mrksich and Whitesides, 1995, Sackmann, 1996). Alternatively, vesicular closed lipid bilayer structures or liposomes can be prepared (New, 1992). A lipid membrane can be regarded as a two-dimensional liquid, in which the lipid molecules and the other molecules like proteins that are associated with it (natural membrane structures such as cell membranes) or have been attached on it, do move relatively freely on the plane of the membrane (lateral diffusion, Tamm, 1988, Glaser, 1993). There are applications which are based on the function of molecules which participate in specific binding and recognition reactions and are attached on lipid membranes (Odashima et al., 1991). This kind of functional lipid membranes have substantial potential as e.g. recognition surfaces in biosensors (Kiefer et al., 1991, Mrksich and Whitesides, 1995). Antibodies that can be generated by using known technology against almost any macromolecule and against numerous smaller molecules (Lerner et al., 1992, Nissim et al., 1994) are particularly interesting as recognition molecules.

We have developed a method for the attachment of bacterially-produced antibodies and other proteins on lipid membranes. The method is based on a so-called biosynthetic lipid-tagging technique (Laukkanen et al., 1993, Keinänen and Laukkanen, 1994), in which a lipid structure is attached on the N-terminal cysteine residue of a antibody-lipoprotein fusion during biosynthesis. This hydrophobic lipid anchors the antibody (protein) on the outer membrane of the bacterium. Likewise, the purified lipid-tagged antibody can be attached on the surface of a liposome, e.g. by using detergent dialysis method (Laukkanen et al., 1994).

Based on what has been described above, we have now developed a novel homogeneous immunoassay method, which enables simple and easy detection of a possible presence, or measurement of the concentration of an analyte in a sample. According to the invention antigens are preferably determined, in which case the receptor molecule to be attached on the lipid membrane is an antibody specific to the analyte.

Our invention originates from the idea that the binding reaction between the antigen in the liquid phase and the antibodies attached on the lipid membrane can be coupled to FRET phenomenon when the antigen is multivalent (FIG. 1). The term "multivalent antigen" used herein refers to an antigen which carries more than one antibody-binding epitopes. The homogeneous immunoassay method according to the invention comprises two lipid-tagged antibody populations on a lipid membrane, with one population labeled with a FRET donor fluorophore and the other population with FRET acceptor fluorophore. When the antibody gets into contact with a multivalent antigen, a patching of the antibodies on the lipid membrane results. There the said antigen brings the acceptor and donor fluorophore-containing antibodies moving freely on the lipid membrane in close contact, in other words, a microaggregation takes place, in which case the energy transfer from the excited donor fluorophore to the acceptor fluorophore may occur (FRET phenomenon). The free lateral mobility of the antibody in immunoliposomes enables the FRET phenomenon. The mobility is achieved by the presence of the lipid anchor which attaches the antibody onto the lipid bilayer. As lipid membranes (e.g. planar membranes) can be attached on the surface of a solid substrate, e.g. by using the Langmuir-Blodgett technique (Mrksich and Whitesides, 1995, Sackmann, 1996), and liposomes can be attached e.g. by using biotin-streptavidin layer technique (Orellana et al., 1996), the invention enables a direct ("homogeneous") immunoassay, which does not contain separate washing and separation steps but only the addition of the sample and the measurement of the signal.

In the measurement the fluorescence is excised in the donor (e.g. using a light source with a suitable wavelength), and the higher amount of the antibodies attached on the membrane are in close contact, the greater part of the excitation energy is transferred to the acceptor and does not discharge directly as the fluorescence characteristic to the donor. The net result is thus decrease of the fluorescence characteristic to the donor and increase of the fluorescence characteristic to the acceptor. In the measurement the fluorescence of the surface in contact with the sample can be compared to a reference surface without a sample, and then either the fluorescence of the donor or the fluorescence of the acceptor, or in most cases their proportion (as the function of time) can be measured. All these are changed when the "aggregation level" of the antibodies on the membrane changes as a consequence of the attachment of the antigen.

Correspondingly, in the presence of a monovalent antigen there is no mechanism in such an assay to bring together the antibody molecules, but these continue to move freely on the lipid membrane, and no FRET phenomenon is observed. It is possible, however, to measure the monovalent antigen indirectly, if a known amount of the same antigen is added to the assay solution, the antigen being converted into a polyvalent form, i.e. having two or more separate antigenic structures, which results in the displacement of the multivalent antigen by the monovalent "free" antigen and thereby in quenching of the FRET phenomenon, whereby the resulting change of fluorescence can be measured.

As the analyte-receptor pair an antibody-antigen pair can also be used instead of an antigen-antibody pair, in which case the antigen is anchored on the lipid membrane and the antibody is in the solution, and the antibody or its amount is measured. Because natural antibodies are always polyvalent, they can always be measured with a direct assay.

Our invention is neither restricted to the use of lipid anchored antibodies prepared by the above described biosynthetic method, as different known techniques are available for the attachment of soluble proteins, in particular, of antibodies to a lipid membrane; fatty acids (Huang et al., 1980, Ho et al., 1986) or other lipids (Heath et al., 1981, Martin et al., 1981) can be coupled covalently to an antibody molecule enabling the anchoring of the antibody to the lipid membrane; alternatively a biotin-containing lipid can be incorporated in the lipid membrane, which then may bind avidin/streptavidin, and further a biotinylated antibody (Loughrey et al., 1987, 1990).

The following non-limiting examples illustrate the invention further. The examples include the preparation, labeling and attachment on the liposomal surface of the lipid-tagged antibody, and the immunoassay performed by using the antibody so obtained.

EXAMPLE 1

Cloning of a Single-chain Lipid-modified Anti-2-phenyloxazolone Antibody (Ox lpp-scFv-H)

In the DNA cloning and modifications standard recombinant methodology was used (Sambrook et al., 1989, Griffin and Griffin, 1994). *Escherichia coli* DH5α strain (F⁻, endA1, hsdR17($r_{k-}$, $m_{k+}$), supE44, thi-1, λ-, recA1, gyrA96, relA1, Δ(argF-lacZYA)U169, φ80dlacZΔM15) was used as a host for the preparation of the recombinant DNA plasmids, and RV308 strain (su⁻, ΔlacX74, galISII::OP308, strA) was used as a host for protein production.

The amino terminal lipoprotein sequences necessary for the lipid modification were amplified by PCR (polymerase chain reaction, Saiki et al., 1988) using pKEN125 plasmid as a template (Laukkanen et al., 1993), and the oligonucleotides 1 and 2 as DNA primers (Table I). Correspondingly the DNA region encoding the single-chain anti-2-phenyloxazolone antibody was amplified by using plasmic pML5 (Takkinen et al., 1991) as a template and the oligonucleotides 3 and 4 as DNA primers (Table I). The DNA primers were synthesized by using Applied Biosystems 391 DNA synthesizer and they were used without further purification.

TABLE I

DNA primers for the cloning of the lipid-modified antibody (Ox lpp-scFv-H). The restriction sites used in the cloning are underlined and the sequence complementary to that present in the template is shown in bold-face type.

Primer 1:   EcoRI

5'-TCAT<u>GAATTC</u>ATGAAAGCTACTAAACTGG-3'   (SEQ ID NO:1)

Primer 2:   BamHI

5'-AAGTAGCTAGC<u>GGATCC</u>CTGATCGATTTTAGCGTTGC-3'   (SEQ ID NO:3)

TABLE I-continued

DNA primers for the cloning of the lipid-modified antibody (Ox lpp-scFv-H). The restriction sites used in the cloning are underlined and the sequence complementary to that present in the template is shown in bold-face type.

Primer 3:                 BamHI

5'-TATGAATTCGCTAGC<u>GGATCC</u>CAGGTGCAGCTGAAGGAGTC (SEQ ID NO:3)

AGG-3'

Primer 4:     HindIII

5'-ACATC<u>AAGCTT</u>CTATTTCAGCTCCAGCTTG-3'        (SEQ ID NO:4)

Primer 5:     HindIII

5'-AAGAT<u>AAGCTT</u>CTAATGATGGTGATGATGATGTTTCAGCTC (SEQ ID NO:4)

CAGCTTGGTCCCAGCACC-3'

The amplified DNA encoding the lipoprotein sequences (114 base pairs, bp) was digested with the restriction enzymes EcoRI and BamHI, and the said DNA fragment was first cloned into a pUC18 vector treated with the same enzymes. Thereafter, the DNA encoding the single-chain antibody (776 bp) was digested with the restriction enzymes BamHI and HindIII and cloned into the lpp-pUC18 vector prepared as described above, and finally, the DNA fragment encoding the Ox lpp-scFv-protein obtained by digestion with EcoRI and HindIII was cloned into pKKtac vector and designated as pML3.7 (Laukkanen et al., 1993).

Figure 1:
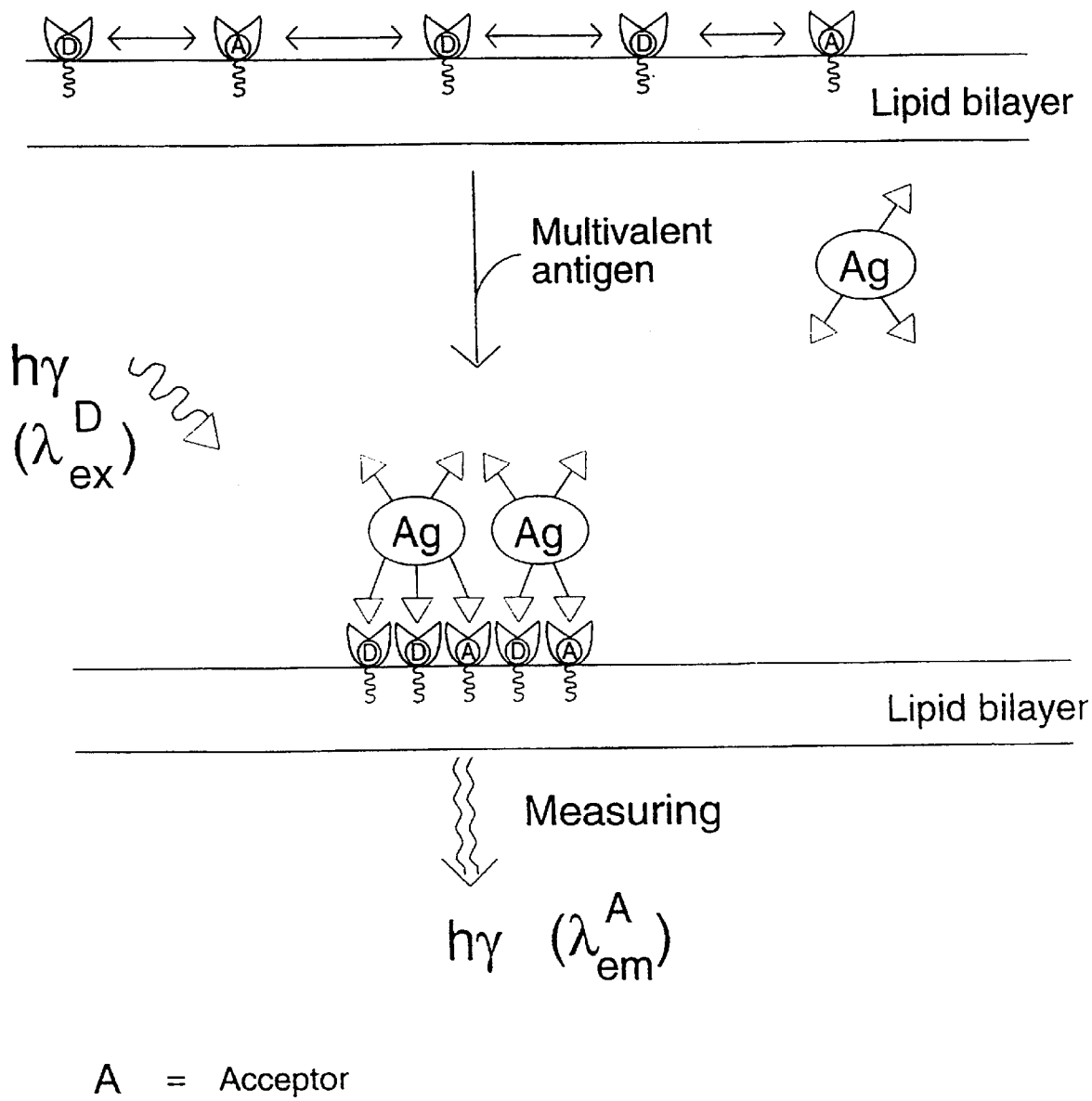
FIG. 1. The principle of the fluorescence energy transfer-based homogeneous immunoassay method.
Figure 2:
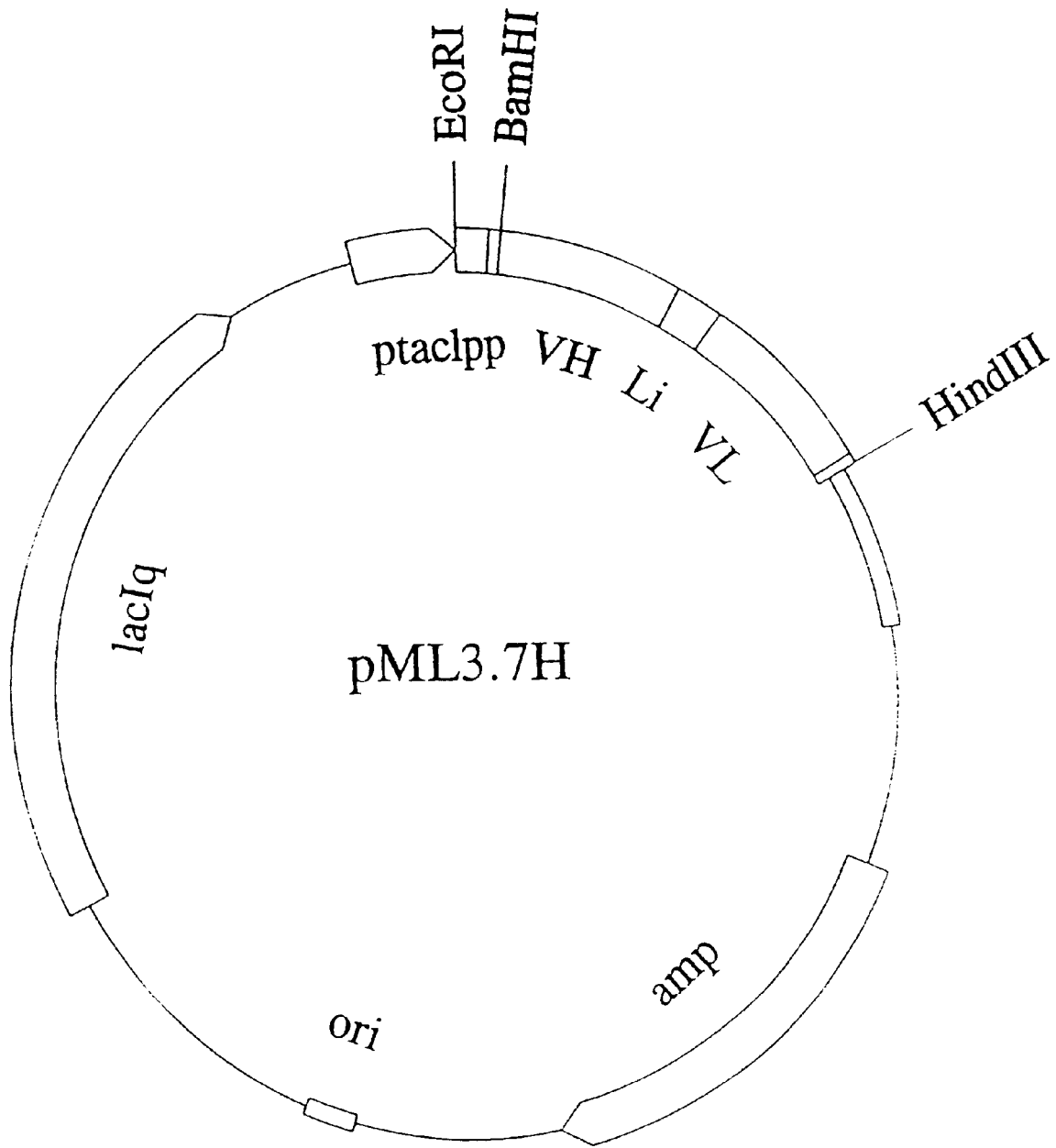
FIG. 2. The bacterial expression vector encoding the lipid-tagged single-chain 2-phenyloxazolone binding antibody, pML3.7H. The most important restriction sites are indicated. The abbreviations used in the figure: ptac—tac promoter region; lpp—lipoprotein; VH—variable region of the antibody heavy chain; Li—linker region; VL—variable region of the antibody light chain; amp—β-lactamase gene; ori—origin of replication of plasmid DNA; laciq—lactose repressor gene.

To facilitate purification, the DNA encoding the Ox lpp-scFv protein was further modified by adding a DNA sequence encoding for six histidines in the C-terminus, by using plasmid pML3.7 as a template and oligonucleotide 5 (Table I) as the DNA-primer of the 3' end. The final recombinant DNA plasmid was designated as pML3.7H (FIG. 2).

The correctness of the amplified DNA sequences was verified by dideoxynucleotide sequencing (Sanger et al., 1977).

EXAMPLE 2

Production of the Antibody Ox lpp-scFv-H in *E. coli*

The production of the antibody in bacterial cells was performed as described in Laukkanen et al. (1993). First, the recombinant DNA plasmid pML3.7H was transferred to the production strain *Escherichia coli* RV308. An *E. coli* pML3.7H/RV308 culture which had been grown shaking for 16–18 hours at +30° C. was then passaged by diluting 1:50 in LB medium (Sambrook et al., 1989), containing 100 µg of ampicillin/ml. The cultivation was continued at +30° C. until the absorbance of the bacterial suspension measured at 600 nm in spectrophotometer reached a value of 1.5, whereafter the production of the recombinant protein was induced by addition of isopropylthio-β-D-galactoside (IPTG) to a final concentration of 1 mM. Thereafter the cultivation was continued for further 16–18 hours at +30° C. Finally the bacterial cells were collected by centrifugation (5000 g, 10 min, +4° C.).

The cell samples were analyzed by SDS-polyacrylamide gel electrophoresis (Laemmli, 1979) and immunoblotting and -staining (Towbin et al., 1979), in which a rabbit antiserum specific to single-chain anti-2-phenyloxazolone antibody (Ox scfv) was used (Takkinen et al., 1991). After the primary antibody, the blots were incubated with alkaline phosphatase-anti-IgG-conjugate and finally, commercial substrates (NBT and BCIP, Promega) were added for the detection of the alkaline phosphatase activity.

An immunoreactive protein of the size (31 kDa) corresponding to what was calculated for the lipid-tagged single-chain antibody was observed after immunoblotting and -staining in samples prepared from induced bacterial cells harboring the plasmid pML3.7H. No immunoreactive protein was observed after immunostaining of samples prepared from bacterial cells harboring the plasmid pKKtac, used as a control. Based on the immunoreactivity, the production level of Ox lpp-scFv-H in said bacteria was about 5 mg/l.

EXAMPLE 3

Purification of the Ox lpp-scFv-H Antibody

The antibody derivative was produced as described above and purified by using both metal chelation affinity chromatography (Porath and Olin, 1983; Hochuli et al., 1988; Smith et al., 1988) and hapten affinity chromatography according to Laukkanen et al. (1994). The bacterial cells harvested from a one-liter culture were suspended in 50 ml of lysis buffer (10 mM HEPES, pH 7.4, 1 mM EDTA, 1 M NaCl, 0.1 mM PMSF). Lysozyme (1–2 mg/ml) was added in the suspension, which was then incubated for 15 minutes at room temperature. Thereafter Triton X-100 was added to a final concentration of 1% (w/v) to solubilize the membrane proteins, and the suspension was stirred for 16–18 hours at +4° C. Thereafter the soluble proteins (including Ox lpp-scFv-H antibody) were separated from the cell lysate by centrifugation (35 000 g, 40 min, +4° C.).

For purification with metal chelation chromatography, the supernatant or the soluble protein fraction was diluted 1:5 in buffer A [10 mM HEPES, pH 7.4, 1 M NaCl, 10% (v/v) glycerol, 0.1 mM PMSF, 1 mM imidazole], the final concentration of Triton X-100 then being 0.2%. To the protein solution (50 ml), 0.5–1 ml of Ni-charged chelating agarose gel (Chelating Sepharose Fast Flow, Pharmacia) was added, and the proteins were allowed to bind to the column material for 16–18 hours under continuous stirring at +4° C. The column material packed into a column was washed with 5–10 ml of buffer A, containing 0.2% (w/v) Triton X-100. The proteins bound to the column material were eluted in 5–10 ml of buffer A, containing 0.2% (w/v) Triton X-100 and 50, 75, 100 and 200 mM imidazole.

Based on immunoreactions (immunoblotting and -staining, see above), the partially purified antibody (31 kDa protein) was eluted in the 75 and 100 mM imidazole fractions which were then combined for the next purification step, affinity chromatography based on immobilized hapten. The final imidazole fraction was diluted 1:5 in buffer B [10 mM HEPES, pH 7.4, 1 M NaCl, 10% glycerol, 0.2% (w/v) Triton X-100], and a 2-phenyloxazolone-BSA conjugate ($Ox_{21}BSA$) (Mäkelä et al., 1978) was coupled to agarose gel (CNBr-activated Sepharose 4B, Pharmacia) according to the manufacturer's instructions. The diluted protein solution and the $Ox_{21}BSA$-Sepharose gel were combined and the proteins were allowed to bind to the gel for 16–18 hours at +4° C. Thereafter the gel was packed into a column and it was washed, and the bound proteins were eluted according to a previously described method (Takkinen et al., 1991) with the exception that the buffers contained 0.2% (w/v) Triton X-100, and upon elution of the antibody by low pH the detergent was replaced by 1% (w/v) OG (n-octyl-β-D-glucopyranoside).

Following the metal chelation affinity chromatography and hapten affinity chromatography purifications, the protein samples were analyzed by using SDS-polyacrylamide gel electrophoresis (see above). In the Coomassie-stained 15% SDS-polyacrylamide gel, an enrichment of a 31-kDa protein was observed after the various steps of the purification. The samples were also analyzed by immunoblotting (see above), and immunoreactivity was found to be due to the 31-kDa protein. From these results, it was concluded that the use of the above-mentioned purification protocol results in the purification of the lipid-tagged antibody.

The hapten-binding activity of the lipid-tagged antibody was determined by using ELISA (enzyme-linked immunosorbent assay) method with microtiter plates coated with 2-phenyloxazolone-BSA-conjugate as described previously (Takkinen et al., 1991; Laukkanen et al., 1993). Demonstration by using ELISA of the specific binding of the antibody to immobilized hapten was performed by adding different amounts of soluble hapten, caproic acid derivative of 2-phenyloxazolone (Ox-CA) or $Ox_{21}BSA$ conjugate (in which every BSA molecule carries on average 21 phenyloxazolone molecules) to the protein samples, resulting in competition of the added hapten of the binding site of the antibody, and therefore displacement of the binding of the Ox lpp-scFv-H antibody to the immobilized hapten-BSA-conjugate.

Generation of the yellow colour reaction ($A_{405}$ was measured) after addition of the substrate for the alkaline phosphatase could be observed in samples containing the purified Ox lpp-scFv-H antibody. In the ELISA analysis in which soluble hapten was used to displace the binding of the antibody, the result obtained was the prevention of the binding of the protein to the immobilized $Ox_{21}BSA$, demonstrating that the protein did specifically bind to the hapten.

Protein concentrations of the purified samples were measured spectrophotometrically ($A_{280}$). The purification of the antibody from cells of a one-liter culture, resulted in 1–2 mg of purified antibody.

EXAMPLE 4

Labeling of the Antibody Ox lpp-scFv-H

Coupling of the fluorescent indicators with the amino groups of the antibody (free aminotermini and the ε-amino groups of lysine residues) was performed according to the manufacture's (Molecular Probes, U.S.A.) instructions with sulfonyl chloride derivative of the Texas Red® fluorophore (T-353) and succinimidyl ester derivative of the fluorescein fluorophore (C-1311).

In the labeling with Texas Red fluorophore, the protein solution purified by metal chelation chromatography was adjusted to 0.1M sodium bicarbonate (pH 9.2), containing 1% (w/v) OG. In the labeling reaction, a ten-fold mass excess of protein (1 mg) over fluorophore (0.1 mg) was used. Texas Red fluorophore was dissolved in a small amount of dimethyl formamide (DMF) and mixed with the protein solution. The labeling reaction was allowed to continue for 16–18 hours at +4° C. protected from light and under shaking. Thereafter the free label was removed by purifying the protein using hapten affinity chromatography as described above (see Example 3). The degree of labeling of the protein was determined according to the formula given by the manufacturer:

$$\frac{A_x}{\epsilon} \times \frac{\text{Molecular weight of the protein (Da)}}{\text{Protein concentration (mg/ml)}} = \frac{\text{Label (mol)}}{\text{Protein (mol)}}$$

in which $A_x$=the absorbance value of the fluorophore measured at the wavelength of absorption maximum, $\epsilon$=the molar extinction coefficient ($\epsilon_{Texas\ Red}$=85 000)

The labeled antibody was purified by hapten affinity chromatography (see above). The absorbance at both 280 nm (protein concentration) and 592 nm (detection of Texas Red fluorophore) of the protein fractions were measured. From the measured values, it could be concluded that the free label did not bind to the column material and was rapidly removed from the sample when the column material was packed into a column and washed as described above. The labeled protein was eluted from the column only in the low pH washes. The said eluted protein was analyzed by SDS-PAGE, in which case the purified protein appeared as a 31-kDa Coomassie-stained band. The protein samples were also analyzed by ELISA, in which the said protein was found to bind to immobilized $OX_{21}BSA$. From the results, it could be stated that the Texas Red fluorophore was coupled to the hapten-binding lipid-tagged antibody.

The labeling of the protein with fluorescein was performed as described above with the exception that the protein was in 0.1 M sodium bicarbonate (pH 8.9), 1% (w/v) OG buffer and the said fluorophore was dissolved in dimethylsulfoxide (DMSO). The labeled protein was analyzed and the degree of labeling was determined as described above ($\epsilon_{fluorescein}$=68000). The lipid-tagged antibody was found to have been labeled also with fluorescein fluorophore.

EXAMPLE 5

Preparation of Immunolinosomes

The purified and labeled Ox lpp-scFv-H antibody was attached to the surface of liposomes by using previously described and generally known methods (New, 1992, Laukkanen et al., 1994). Five milligrams of a mixture of egg yolk phospholipids (phosphatidylcholine, PC; phosphatidylethanolamine, PE) and cholesterol (Cho) (in molar ratio PC:PE:Cho 10:1:5) was dissolved in 5 ml of solution containing 40 μg of purified Ox lpp-scFv-H and 1% (w/v) OG in 10 mM HEPES (pH 7.4) buffer. As controls, liposomes with no added protein were prepared in an otherwise identical manner. The detergent was removed from the clear solution by dialysis against 10 mM HEPES (pH 7.4) buffer solution, by using a LIPOSOMAT dialyzer (Dianorm, Germany) with cellulose membranes (cut-off 10 kDa). After removal of the detergent, the sample was found to be slightly opalescent, suggesting that immunoliposomes had been formed upon removal of the detergent. The opalescent solution was subjected to ultracentrifugation (150 000 g, 1 h, +4° C.) which was found to result in the formation of a pellet in the bottom of the centrifugation tube, which was then suspended in 1–2 ml of 10 mM HEPES (pH 7.4) buffer. The liposomes and immunoliposomes were stored at +4° C. as suspensions.

The pellet was analyzed by electron microscopy as described in Laukkanen et al., 1994. A sample drop was dried on carbon-coated copper grid (150–200 mesh) and stained with 1% potassium phosphotungstate (pH 7.4). The sample was analyzed by using a transmission electron microscope (Jeol JEM-100CX) at 60V. In the sample, lipsomes with a diameter of 100–200 nm were observed. In addition, the supernatant and pellet from the ultracentrifugation were analyzed by immunoblotting (see above). In the pellet sample, a 31-kDa immunoreactive band was observed, whereas no immunoreactivity was present in the supernatant sample. The samples were also analyzed by using ELISA (see above), in which the pellet was found to contain hapten-binding activity. The results indicate that the pellet contains the hapten-binding lipid-tagged antibody as anchored to liposomes.

Alternatively, immunoliposomes were prepared by rapid dilution of the sample which contained a detergent with a high so called critical micelle concentration (CMC) to a concentration which is below the CMC, resulting in the binding of the hydrophobic protein on the membrane of the liposomes, the protein being retained soluble by the detergent (New, 1992, Laukkanen et al., 1995). Ox lpp-scFv-H antibody [40 $\mu$g of protein in 10 mM HEPES, pH 7.4, 0.7% (w/v) OG solution] was mixed with a liposome preparation containing 5 mg phospholipid-cholesterol mixture ($V_{tot}$=5 ml). The mixture, containing OG at a final concentration of 0.02%, was stirred for 16–18 hours at +4° C. Thereafter the immunoliposomes were harvested by ultracentrifugation as described above.

EXAMPLE 6

Fluorescence-based Immunoassay of Multivalent Antigen

Immunoliposomes were prepared as in Example 3, with the exception that the antibody consisted of two preparations labeled with different fluorophores and mixed in mass ratio 1:1 before the preparation of liposomes. Half of the antibody molecules were labeled with fluorescein and the other half with Texas Red fluorophore. This results in immunoliposomes which have statistically 50% fluorescein-labeled and 50% Texas Red-labeled antibody. For control experiments, liposomes containing only fluorescein or only Texas Red-labeled antibody were prepared. The fluorescence of the prepared fluorescent immunoliposomes was measured in Shimadzu FR-5000 spectrofluorometer in a quartz cuvette in 10 mM HEPES, pH 7.4 buffer. The fluorescence of fluorescein was excited at a wavelength of 492 nm and the emission was measured at a wavelength of 516 nm, whereas for Texas Red the excitation wavelength was 596 nm, and the emission energy was measured at a wavelength of 620 nm. Alternatively, the fluorescence emission spectrum was recorded in the wavelength range of 500–700 nm. With an excitation wavelength of 492 nm, a strong fluorescence was observed in the fluorescein/Texas Red liposome preparation at the fluorescein emission maximum, and only a very weak fluorescence at 620 nm, whereas with an excitation wavelength of 596 nm, a strong fluorescence was recorded at the emission maximum of Texas Red (620 nm). Control liposomes, containing only fluorescein or only Texas Red-labeled antibody, produced only fluorescence spectra typical for each of the used fluorophores.

The fluorescein/Texas Red-labeled immunoliposome preparation described above was excited at 492 nm, and the emission was recorded at two wavelegths, 516 nm (fluorescein) and 620 nm (Texas Red) in a continuous fashion in a cuvette equipped with a magnetic stirrer. When the multivalent antigen, $OX_{16}BSA$, was added an increase of fluorescence at 620 nm, and a decrease of fluorescence at 516 nm was observed. In control experiments where soluble hapten, a caproic acid-derivative of phenyloxazolone, or BSA alone, were added in the liposome preparation instead of $OX_{16}BSA$, no such a change in the fluorescence was observed. When in a similar experiment liposomes were used which contained only the fluoresce-inlabeled antibody, a slight decrease in the fluorescence at 516 nm was correspondingly observed after addition of $OX_{16}BSA$ (but no fluorescence at 620 nm). When liposomes labeled only with Texas Red were used, no observable fluorescence was measured at 516 nm or at 620 nm with an excitation wave-length of 492 nm. Therefore, the addition of a multivalent antigen in the liposome preparation caused a specific fluorescence signal (Table II).

The observation can be explained in terms of fluorescence resonance energy transfer so that the binding of the multivalent hapten ($OX_{16}BSA$) causes the aggregation of labeled antibody molecules on the surface of the liposomes, whereupon the excitation energy of fluorescein fluorophore (donor) can directly be transferred to excite a fluorescence in Texas Red (acceptor). Consequently, the fluorescence emission of Texas Red (620 nm) is increased, whereas the emission of fluorescein (516 nm) is decreased, because part of its excitation energy is dissipated in mechanisms other than its own fluorescence (quenching).

TABLE II

THE FLUORESCENCE CHANGES IN THE LIPOSOME PREPARATIONS AT EXCITATION WAVELENGTH OF 492 nm.

Explanation of the symbols and abbreviations: F/TXR: liposomes containing both fluorescein and Texas Red-labeled antibody; F: liposomes containg only fluorescein-labeled antibody; TXR: liposomes containing only Texas Red-labeled antibody; ↑, an increase in fluorescence; ↓, a decrease in fluorescence; –: no change in fluorescence; $OX_{16}BSA$, phenyloxazolone-BSA conjugate; OX, caproic acid derivative of phenyloxazolone.

| Liposomes | Sample added | Fluorescence (516 nm) | Fluorescence (620 nm) |
|---|---|---|---|
| F/TXR | $OX_{16}BSA$ | ↓ | ↑ |
|  | BSA | – | – |
|  | OX | – | – |
| F | $OX_{16}BSA$ | ↓ | – |
| F | OX | – | – |
| TXR | $OX_{16}BSA$ | – | – |

EXAMPLE 7

Fluorescence-based Immunoassay of a Monovalent Hapten

The experimental setup described in Example 6 can be used in an indirect way as an assay for a monovalent hapten, caproic acid-derivative of 2-phenyloxazolone. $Ox_{16}BSA$ was added in the presence of free soluble hapten in an fluorescein/Texas Red-labeled immunoliposome preparation. A decrease in the fluorescence changes ($\lambda_{em}$ 516 nm ↓, $\lambda_{em}$ 620 nm ↑) proportional to the amount of added free hapten was then observed. A displacement of the multivalent antigen caused by the free hapten was also observed in experiments in which the multivalent antibody was added in the liposomes prior to the hapten.

REFERENCES

Arya, A., Krull, U. J., Thompson, M. and Wong, H. E. (1985) Langmuir-Blodgett deposition of lipid films on hydrogel as a basis for biosensor development. Anal. Chim. Acta 173: 331–336.

Barnard, S. M. and Walt, D. R. (1991) Chemical sensors based on controlled-release polymer systems. Science 251: 927–929.

Clegg, R. M. (1995) Fluorescence resonance energy transfer. Curr. Opin. Biotechnology 6: 103–110.

Glaser, M. (1993) Lipid domains in biological membranes. Curr. Opin. Struct. Biol. 3: 475–481.

Griffin, H. G. and Griffin, A. M. (1994) PCR technology. Current innovations. CRC Press Inc., Boca Raton, Fla., U.S.A.

Heath, T. D., Macher, B. A. and Papahadjopoulos, D. (1981) Covalent attachment of immunoglobulins to liposomes via glycosphingolipids. Biochem. Biophys. Acta 640: 66–81.

Hemmilä, I. (1991) Application of fluorescence in immunoassays. Wiley-Interscience, New York, U.S.A.

Ho, R. J. Y., Rouse, B. T. and Huang, L. (1986) Target-sensitive immunoliposomes: preparation and characterization. Biochemistry 25: 5500–5506.

Hochuli, E., Bannwarth, W., Döbeli, H., Gentz, R. and St über, D. (1988) Genetic approach to facilitate purification of recombinant proteins with novel metal chelate adsorbent. Bio/Techology 6: 1321–1325.

Huang, A., Huang, L. and Kennel, S. J. (1980) Monoclonal antibody covalently coupled with fatty acids. A reagent for in vitro liposome targeting. J. Biol. Chem. 225: 8015–8018.

Keinänen, K. and Laukkanen, M.-L. (1994) Biosynthetic lipid-tagging of antibodies, FEBS. Lett. 346: 123–126.

Kiefer, H., Klee, B., John, E., Stierhof Y.-D. and Jähnig (1991) Biosensors based on membrane transport proteins. Biosensors & Bioelectronics 6: 233–237.

Kricka, L. J. (1994) Selected strategies for improving sensitivity and reliability of immunoassays. Clin. Chem. 40: 347–357.

Laemmli, U. K. (1970) Cleavage of structural proteins during the assembly of the head of the bacteriophage T4. Nature 222: 680–685.

Laukkanen, M.-L., Alfthan, K. and Keinänen, K. (1994) Functional immunoliposomes harboring a biosynthetically lipid-tagged single-chain antibody. Biochemistry 33: 11664–11670.

Laukkanen, M.-L., Orellana, A. and Keinänen, K. (1995) Use of genetically engineered lipid-tagged antibody to generate functional europium chelate-loaded liposomes: application in fluoroimmunoassay. J. Immunol. Methods 185: 95–102.

Laukkanen, M.-L., Teeni, T. T. and Keinänen, K. (1993) Lipid-tagged antibodies: bacterial expression and characterization of a lipoprotein-single-chain antibody fusion protein. Protein Eng. 6: 449–454.

Lerner, R. A., Kang, A. S., Bain, J. D., Burton, D. R. and Barbas, III C. F. (1992) Antibodies without immunization. Science 285: 1313–1314.

Loughrey, H. C., Bally, M. B. and Cullis, P. R. (1987) A non-covalent method of attaching antibodies to liposomes. Biochem. Biophys. Acta 910: 157–160.

Loughrey, H. C., Choi, L. S., Cullis, P. R. and Bally, M. B. (1990) Optimized procedure for the coupling of proteins to liposomes. J. Immunol. Methods 132: 25–35.

Martin, F. J., Hubbell, W. L. and Papahadjopoulos, D. (1981) Immunospecific targeting of liposomes to cells: A novel and efficient method for covalent attachment of Fab' fragments via disulfide bonds. Biochemistry 20:4229–4238.

Mergny, J.-L., Boutorine, A. S., Garestier, T., Belloc, F., Rougée, M., Bulychev, N. V., Koshkin, A. A., Bourson, J., Lebedev, A. V., Valeur, B., Thuong, N. T. and Hélène, C. (1994) Fluorescence energy transfer as a probe for nucleic acid structures and sequences. Nucleic Acids Res. 22: 920–928.

Mrksich, M and Whitesides, G. M. (1995) Patterning self-assembled monolayers using microcontact printing: a new technology for biosensors? TIBTECH 13: 228–235.

Mäkelä, O., Kaartinen, M., Pelkonen, J. K. and Karjalainen, K. (1978) Inheritance of antibody specificity V. Anti-2-phenyloxazolone in the mouse. J. Exp. Med. 148: 1644–1660.

New, R. R. C. (1992) Preparation of liposomes, In: New, R. R. C. (ed.) Liposomes, a practical approach. Oxford University Press, Oxford, U.K., pages 33–104.

Nissim,, A., Hoogenboom, H. R., Tomlinson, I. M., Flynn, G., Midgley, C., Lane, D. and Winter, G. (1994) Antibody fragments from a "single pot" phage display library as immunochemical reagents. EMBO J. 13: 692–698.

Odashima, K., Sugawara, M. and Umezawa, Y. (1991) Biomembrane mimetic sensing chemistry. Trends Anal. Chem. 10: 207–215.

Orellana, A., Laukkanen, M.-L. and Keinänen, K. (1996) Europium chelate-loaded liposomes: a tool for the study of binding and integrity of liposomes. Biochem. Biophys. Acta, in press.

Pinnaduwage, P. and Huang, L. (1992) Stable target-sensitive immunoliposomes. Biochemistry 31:2850–2855.

Porath, J. and Olin, B. (1983) Immobilized metal ion affinity adsorption and immobilized metal ion affinity chromatography of biomaterials. Serum protein affinities for gel-immobilized iron and nickel ions. Biochemistry 22: 1621–1630.

Sackmann, E. (1996) Supported membranes: scientific and practical applications. Science 271: 43–48.

Saiki, R. K., Gelfand, D. H., Stoffel, S., Scharf, S. J., Higuchi, R., Horn, G. T., Mullis, K. B. and Erlich, H. A. (1988) Primer directed enzymatic amplification of DNA with thermostable DNA polymerase. Science 239: 478–491.

Sambrook, J., Fritsch, E. F. and Maniatis, T. (1989) Molecular cloning: a laboratory manual. 2nd edition. Cold Spring Harbor Laboratory Press, Cold Spring Harbor, N.Y., U.S.A.

Sanger, F., Nickel, S. and Coulson, A. R. (1977) DNA sequencing with chain terminating inhibitors. Proc. Natl. Acad. Sci. U.S.A. 74: 5463–5467

Selvin, P. R. (1995) Fluorescence resonance energy transfer. Meth. Enzymol. 246: 300–334.

Smith, M. C., Furman, T. C., Ingolia, T. D. and Pidgeon, C. (1988) Chelating peptide-immobilized metal ion affinity chromatography. A new concept in affinity chromatography for recombinant proteins. J. Biol. Chem. 263: 7211–7215.

Takkinen, K., Laukkanen, M.-L., Sizmann, D., Alfthan, K., Immonen, T., Vanne, L., Kaartinen, M. and Teeri, T. T. (1991) An active single-chain antibody containing a cellulase linker domain is secreted by *Escherichia coli*. Protein Eng. 4: 837–841.

Tamm, L. K., (1988) Lateral diffusion and fluorescence microscope studies on a monoclonal antibody specifically bound to supported phospholipid bilayers. Biochemistry 27: 1450–1457.

Towbin, H., Staehelin, T. and Gordon, J. (1979) Electrophoretic transfer of proteins from polyacrylamide gels to nitrocellulose sheets: procedure and some applications. Proc. Natl. Acad. Sci. U.S.A. 76: 4350–4354.

Waggoner, A. (1995) Covalent labeling of proteins and nucleic acids with fluorophores. Meth. Enzymol. 246: 362–373.

Watts, T. H., Gaub, H. E. and McConnell, H. M. (1986) T-cell-mediated association of peptide antigen and major histocompatibility complex protein detected by energy transfer in an evanescent wave-field. Nature 320: 179–181.

Zasadzinski, J. A., Viswanathan, R., Madsen, L., Garnaes, J. and Schwartz, D. K. (1994) Langmuir-Blodgett films. Science 263: 1726–1733.

---

What is claimed is:

1. A fluorescence-based immunoassay method for the detection of an analyte or for the determination of its concentration in a sample, comprising:

attaching receptor molecules specific for said analyte, one part of the molecules being labeled with a first fluorophore acting as a donor and another part with a second fluorophore acting as an acceptor, to a lipid membrane on a plane of which they are able to move freely;

bringing the sample possibly containing said analyte into contact with said receptor molecules; and measuring the fluorescence change caused by a change of an aggregation level of the receptor molecules on the membrane as a consequence of the attachment of the analyte.

2. The method according to claim 1, wherein the analyte is an antigen and the receptor is an antibody.

3. The method according to claim 2, further comprising adding to the antigen-containing sample a known amount of molecules having two or more separate antibody-binding antigen structures when the analyte is a monovalent antigen.

4. The method according to claim 1, wherein the analyte is an antibody and the receptor is an antigen.

5. The method according to claim 1, wherein the lipid membrane is in the form of a liposome.

6. The method according to claim 1, wherein the lipid membrane is in the form of a planar membrane.

7. The method according to claim 1, wherein the receptor molecules are attached to the lipid membrane via lipid molecules, the receptor molecules are attached to the lipid molecules chemically or by genetic engineering.

8. The method according to claim 1, wherein fluorescein or its derivative is used as a fluorescence donor and rhodamine or its derivative as an acceptor.

9. The method according to claim 2, wherein the antigen to be assayed contains at least two epitopes.

10. The method according to claim 9, wherein said at least two epitopes are different.

11. The method according to claim 9, wherein said at least two epitopes are identical.

* * * * *

SEQUENCE LISTING

<160> NUMBER OF SEQ ID NOS: 5

<210> SEQ ID NO: 1
<211> LENGTH: 29
<212> TYPE: DNA
<213> ORGANISM: Artificial Sequence
<220> FEATURE:
<223> OTHER INFORMATION: Description of Artificial Sequence: DNA primer
      for the cloning of the lipid-modified antibody (Ox 1pp-scFv-H)

<400> SEQUENCE: 1
tcatgaattc atgaaagcta ctaaactgg                                    29

<210> SEQ ID NO: 2
<211> LENGTH: 37
<212> TYPE: DNA
<213> ORGANISM: Artificial Sequence
<220> FEATURE:
<223> OTHER INFORMATION: Description of Artificial Sequence: DNA primer
      for the cloning of the lipid-modified antibody (Ox 1pp-scFv-H)

<400> SEQUENCE: 2
aagtagctag cggatccctg atcgatttta gcgttgc                           37

<210> SEQ ID NO: 3
<211> LENGTH: 44
<212> TYPE: DNA
<213> ORGANISM: Artificial Sequence
<220> FEATURE:
<223> OTHER INFORMATION: Description of Artificial Sequence: DNA primer
      for the cloning of the lipid-modified antibody (Ox 1pp-scFv-H)

<400> SEQUENCE: 3
tatgaattcg ctagcggatc ccaggtgcag ctgaaggagt cagg                   44

<210> SEQ ID NO: 4
<211> LENGTH: 30
<212> TYPE: DNA
<213> ORGANISM: Artificial Sequence
<220> FEATURE:
<223> OTHER INFORMATION: Description of Artificial Sequence: DNA primer
      for the cloning of the lipid-modified antibody (Ox 1pp-scFv-H)

<400> SEQUENCE: 4
acatcaagct tctatttcag ctccagcttg                                   30

```
<210> SEQ ID NO: 5
<211> LENGTH: 59
<212> TYPE: DNA
<213> ORGANISM: Artificial Sequence
<220> FEATURE:
<223> OTHER INFORMATION: Description of Artificial Sequence: DNA primer
      for the cloning of the lipid-modified antibody (Ox 1pp-scFv-H)

<400> SEQUENCE: 5
aagataagct tctaatgatg gtgatgatga tgtttcagct ccagcttggt cccagcacc      59
```